United States Patent
Bernhardt

(10) Patent No.: US 6,831,086 B1
(45) Date of Patent: *Dec. 14, 2004

(54) PROCESS FOR THE INACTIVATION OF VIRUSES WITH THE AID OF ACRIDINE DERIVATIVES

(75) Inventor: Dieter Bernhardt, Cölbe (DE)

(73) Assignee: ZLB Behring GmbH, Marburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 816 days.

(21) Appl. No.: 08/568,820

(22) Filed: Dec. 7, 1995

(30) Foreign Application Priority Data

Dec. 10, 1994 (DE) .......................................... 44 44 045

(51) Int. Cl.[7] .............................................. A61K 31/44
(52) U.S. Cl. ...................................................... 514/297
(58) Field of Search ......................................... 514/297

(56) References Cited

U.S. PATENT DOCUMENTS 5,559,250 A * 9/1996 Cook et al. ................. 549/282
5,691,132 A * 11/1997 Wollowitz et al. ............. 435/2

FOREIGN PATENT DOCUMENTS

EP 0 196 515 10/1986

OTHER PUBLICATIONS

CAPLUS Abstract, AN 1965:92950, 1965, Falcoff et al.*
CAPLUS Abstract, AN 1965:492013, 1965, Coto et al.*
CAplus Abstract, AN 1973:473648, Glaz et al., 1973.*
Armstrong et al., "Inactivation of Viruses by Benzalkonium chloride," 1964, Applied Microbiology, V ol. 12, No. 2, pp. 132–137.*
Wainberg et al. "Inactivation of human immunodeficiency virus type 1 in tissue culture fluid and in ginital secretions by the spermicide benzalkonium chloride," 1990, J. Clinical microbiology, vol. 28, 1, pp. 156–158.*
HCAPLUS Abstract AN: 1991: 639679, Suzuki et al. (1990).*
WPIDS Abstract AN 86: 266335, Dolana, (1986).*
Suzuki et al., "Quantitative Evaluation of the Inactivation of Human Immunodeficiency Virus (HIV) by Antiseptics for the Oral Cavity", *The Bulletin of the Yamaguchi Medical School*, vol. 37, Nos. 3–4, Dec. 1990, pp. 95–100.

* cited by examiner

*Primary Examiner*—Shengjun Wang
(74) *Attorney, Agent, or Firm*—Finnegan, Henderson, Farabow, Garrett & Dunner, L.L.P.

(57) ABSTRACT

The invention relates to the use of acridine or acridine derivatives, preferably in combination with benzalkonium chloride, for the inactivation of enveloped or nonenveloped viruses. The process according to the invention is preferably carried out in the presence of proteins whose biological activity is substantially retained.

23 Claims, No Drawings

PROCESS FOR THE INACTIVATION OF VIRUSES WITH THE AID OF ACRIDINE DERIVATIVES

This application claims foreign priority of Fed. Rep. Germany application P44440456, filed Dec. 10, 1994.

FIELD OF THE INVENTION

The invention relates to the use of acridine or acridine derivatives, preferably in combination with benzalkonium chloride, for the inactivation of enveloped or nonenveloped viruses. The process according to the invention is preferably carried out in the presence of proteins whose biological activity is largely retained.

BACKGROUND OF THE INVENTION

It has been known for years that untreated human plasma or serum can contain human pathogenic viruses, such as HIV, HBV or HCV, which, if transmitted to sensitive recipients, can cause serious diseases, such as AIDS or hepatitis. In order to prevent this potential virus transmission, therapeutics which are obtained from human plasma or serum are prepared, on the one hand, only from preselected starting materials which, as far as anyone can judge, are virus-free and, on the other hand, are subjected to virus-inactivating/eliminating steps in the preparation process. The efficiency of the virus inactivation/elimination method used is established using strict measures and continuously checked.

Besides physical virus inactivation steps, chemical virus inactivation steps are also known in the preparation of said therapeutics. A particularly frequently discussed chemical process is the SD (solvent/detergent) method. It is suitable for inactivating enveloped viruses, i.e. viruses which are surrounded by a lipid-containing membrane, but has the crucial disadvantage of being completely ineffective against all known nonenveloped (uncoated) viruses. Moreover, also no other chemical process is known which would be suitable to inactivate nonenveloped viruses while simultaneously retaining the biological activity of the protein constituents of the therapeutic or of the human plasma or serum.

Although the chemical virus inactivation processes are only used in a supplementary capacity to the physical methods, and although most viruses potentially transmissible by blood and blood products carry a lipid coat, for reasons of safety there is an exceptional need to make available chemical inactivation processes which also reliably inactivate nonenveloped viruses. This is all the more desirable as recently also HAV and parvoviruses, for example parvovirus B 19, were discussed as viruses which are potentially transmissible by blood fluids or blood products. (Vox Sanguinis 67, Supplement 1, 1994: Proceedings of a Symposium held at the New York Blood Center).

The invention was also based on the object of developing an industrially utilizable process for chemical virus inactivation, in which enveloped and nonenveloped viruses, e.g. parvo viruses, are inactivated with retention of the biological activity of proteins present, e.g. therapeutically useful proteins.

SUMMARY OF THE INVENTION

This object is achieved according to the invention by adding acridine or an acridine derivatives to the protein-containing liquid to be treated. It was surprisingly found that acridine or acridine derivatives inactivate enveloped and nonenveloped viruses. Acridine derivatives are, for example, ethacridine, 9-aminoacridine (=amina-crine), 3,6-acridinediamine (proflavine), acrisorcin, Acrizane chloride (=phenacridane chloride), Acridine Orange, quinacrine, acricide, acridone, acridine-9-carboxylic acid, acranil (1-[(6-chloro-2-methoxy-9-acridinyl)amino]-3-(diethylamino)-2-propanol dihydro-chloride), 3,7-diamino-5-phenylphenazinium chloride (phenosafranin, Safranin B Extra), phenoxazine, phenothiazine and especially acriflavine (3,6-diamino-10-methylacridinium, chloride and 3,6-acridineidiamine) and their salts, e.g. chlorides, sulfates, bromides.

Surprisingly, it was additionally found that a combination of acridine or an acridine derivative and benzalkonium chloride displays a synergistic action during virus inactivation, i.e. the magnitude of the virus inactivation of the combination is higher than that of each individual substance.

The virus inactivation process according to the invention can be carried out with protein solutions such as blood, serum, plasma, blood products, allantoic fluid or milk. The virus inactivation is carried out at a pH of 3 to 10 or 5 to 9 (in, for example, serum or plasma solutions) and a temperature of 1° C. to 80° C., preferably of 20° C. to 60° C., very preferably from 20° C. to 40° C. or 25° C. to 37° C., and lasts 30 minutes to 10 hours, preferably 2 to 5 hours. For virus inactivation, a concentration of 1.0 g/l–0.00001 g/l or 1.0 g/l–0.004 g/l, preferably 0.1 g/l–0.001 g/l, is used for the acridines or acridine derivatives, and a concentration of 0.1 g/l–0.004 g/l, preferably 0.05 g/l–0.01 g/l, for benzalkonium chloride.

The removal of the acridines and of the benzalkonium chloride from the protein solutions, if this is necessary, is possible by means of simple, known methods, such as adsorption on active carbon or dialysis.

A further advantage of the virus inactivation process according to the invention is the very extensive protection of the protein constituents of the material to be treated: different biological activities, e.g. antibody activity and clotting-activity, are not reduced or only reduced to a tolerable extent.

The virus inactivation process according to the invention can therefore be employed, for example, for the decontamination of the following materials:

protein-containing solutions (dilute or concentrated)
blood or blood products; both the liquid and the cellular constituents
serum, plasma
allantoic fluid
organ extracts
milk
buffer solutions
antigens for diagnostics
vaccines, antigens for vaccines The process according to the invention is furthermore suitable for disinfection in virus contamination of, for example, areas, equipment, effluents, wastes and surfaces of all types. The disinfection of virus-contaminated organ transplants, e.g. cornea, cerebral meninges, liver, heart, lungs or kidneys is also possible.

DETAILED DESCRIPTION OF THE INVENTION

The present invention is furthermore illustrated by the following examples.

Methods generally used in the process according to the invention

Virus: Was replicated in a known manner in tissue cultures; the virus harvests were centrifuged and used as starting material for the further investigations.

The infectiousness titer was determined in microtiter plates—8 replicates of 0.1 ml/-dilution stage—by double titration.

| Stock solutions: | Ethacridine lactate (EL) | 3% strength in dist. water) |
|---|---|---|
| | Entozon ® (E) | 3% strength Acridines in dist. water} |
| | Acriflavine (A) | 1% strength in dist. water) |
| | Benzalkonium chloride (BACl) | 10% in dist. water |

General experimental procedure:

9 parts of buffer or medium or protein solutions were mixed with 1 part of virus. The addition of the amounts of the stock solutions indicated in the individual examples for virus inactivation and renewed mixing with subsequent virus titration were then carried out. After the times and temperatures mentioned in the individual examples, samples were removed and titrated in double determinations in order to be able to measure the process-related virus inactivation.

Types of virus investigated

| Abbreviation | Name |
|---|---|
| $PI_3V$ | Bovine parainfluenza 3 virus |
| BPV | Bovine parvovirus |
| PPV | Porcine parvovirus |
| IBRV | Infectious bovine rhinotracheitis virus |
| BVDV | Bovine viral diarrhoea virus |
| CPV | Canine parvovirus |
| BAV-1 | Bovine adenovirus type 1 |
| Reo 3 | Reovirus type 3 |
| Influenza A | Influenza A virus-Shangdong |
| Influenza B | Influenza B virus - B Panama |

Further abbreviations/names used in the text:

| EME Medium | Eagles Minimum Essential Medium |
|---|---|
| Beriate ® P | Clotting factor VIII:C concentrate, Pasteurized (Behringwerke AG, Marburg, Germany) |
| Haemate ® P | Concentrate from clotting factor VIII and Von-Willebrand factor, pasteurized (Behringwerke AG, Marburg, Germany) |
| Beriplex ® P | pasteurized prothrombin complex concentrate (Behringwerke AG, Marburg, Germany) |
| Venimmun ® | Human polyvalent immunoglobulin preparation (7S) for intravenous use (Behringwerke AG, Marburg, Germany) |
| Entozon ® | Preparation of the following composition: 1 g of granules contains 0.059 g of dimethoxy-6-nitro-9-[(3-diethylamino-2-hydroxy)propylamino]acridine dihydrochloride and 0.295 g of ethacridine lactate (ASID Veterinär Vertriebs GmbH) |
| QAE cellulose | Diethyle-2-hydroxypropylaminoethyl cellulose (Ion exchanger for protein purification) |
| FCS | Fetal calf serum |

Example 1

Inactivation of $PI_3V$ by BACl

EME medium was mixed with $PI_3$ virus and BACl and incubated at 37° C. in a water bath. After the times indicated, samples were taken to test for virus inactivation. The results are shown in Tab. 1.

TABLE 1

Inactivation of $PI_3$ virus with BACl at 37° C.

| Time (h) | BACl addition (mg/ml) | Virus titer found ($log_{10}$/ml) | Virus inactivation ($log_{10}$/ml) |
|---|---|---|---|
| 0–0.03[1)] | 0 (control) | 7.4 | — |
| | 0.1 | ≦1.5 | ≧5.9 |
| | 0.005 | ≦1.5 | ≧5.9 |
| | 0.025 | 6.0 | 1.4 |
| | 0.0125 | 6.9 | 0.5 |
| 1 | 0 (control) | 6.8 | — |
| | 0.1 | ≦1.5 | ≧5.3 |
| | 0.05 | ≦1.5 | ≧5.3 |
| | 0.025 | ≦1.5 | ≧5.3 |
| | 0.0125 | 5.5 | 1.3 |

[1)]Identical after addition of BACl and thorough mixing of the reaction batch

As emerges from the results in Table 1, $PI_3$ virus is very rapidly inactivated by the high doses of BACl (0.1 mg/ml, 0.05 mg/ml), i.e. in the time which was needed to mix the virus-containing sample thoroughly with BACl, to take a sample and to titrate this in order to determine the infectiousness of $PI_3$ virus, infectious virus was no longer detectable. At the two other BACl concentrations tested (0.025 mg/ml and 0.0125 mg/ml), a clear concentration-time dependence of virus inactivation is discernible.

Example 2

Virus Inactivation by Means of BACl or Entozon

The virus species shown in Tab. 2 were treated with BACl or Entozon and incubated at 45° C. Sample taking for virus titration was-carried out 1 or 2 hours after the start of the test.

TABLE 2

Virus inactivation by means of BACl or Entozon at 45° C.

| Virus | Time | Substance Addition | (mg/ml) | Virus titer found ($log_{10}$/ml) | Virus inactivation ($log_{10}$/ml) |
|---|---|---|---|---|---|
| BPV | 1 hour | Control | 0 | 4.7 | 0 |
| | | BACl | 0.05 | 5.2 | 0 |
| | | BACl | 0.01 | 5.2 | 0 |
| | 2 hours | Control | 0 | 4.6 | 0 |
| | | BACl | 0.05 | 4.6 | 0 |
| | | BACl | 0.01 | 4.6 | 0 |
| | 1 hour | Control | 0 | 4.7 | 0 |
| | | Entozon | 0.030 | ≦1.5 | ≧3.2 |
| | | Entozon | 0.015 | ≦1.5 | ≧3.2 |
| | 2 hours | Control | 0 | 4.6 | 0 |
| | | Entozon | 0.030 | ≦1.5 | ≧3.1 |
| | | Entozon | 0.015 | ≦1.5 | ≧3.1 |
| PPV | 1 hour | Control | 0 | 5.6 | 0 |
| | | Entozon | 0.030 | 3.3 | 2.3 |
| | | Entozon | 0.015 | 3.7 | 1.9 |
| | 2 hours | Control | 0 | 5.6 | 0 |
| | | Entozon | 0.030 | 2.2 | 3.4 |
| | | Entozon | 0.015 | 2.7 | 2.9 |

As the results in Table 2 show, BPV is not inactivated by BACl under the test conditions selected. Inactivation is possible by means of Entozon, inactivation with BPV taking place substantially more rapidly than with PPV.

Example 3
Virus Inactivation by Means of BACI and Acriflavine

The suspensions of the virus species shown in Tab. 3 were treated with BACI or acriflavine and incubated at 37° C. for 2 hours. Samples were then taken for titration to determine the virus inactivation.

TABLE 3

| Virus | Substance addition | (mg/ml) | Virus titer found ($\log_{10}$/ml) | Virus inactivation ($\log_{10}$/ml) |
|---|---|---|---|---|
| IBRV | Control | 0 | 5.1 | 0 |
|  | BACI | 0.01 | ≦1.5 | ≧3.6 |
|  | Acriflavine | 0.001 | 1.8 | 3.3 |
| PI$_3$V | Control | 0 | 5.6 | 0 |
|  | BACI | 0.01 | ≦1.5 | ≧4.1 |
|  | Acriflavine | 0.001 | 3.2 | 2.4 |
| BVDV | Control | 0 | 6.2 | 0 |
|  | BACI | 0.01 | 2.3 | 3.9 |
|  | Acriflavine | 0.001 | 2.5 | 3.7 |
| BPV | Control | 0 | 5.4 | 0 |
|  | BACI | 0.01 | 5.9 | 0 |
|  | Acriflavine | 0.001 | ≦1.5 | ≧3.9 |

As the results in Table 3 show, the enveloped virus species—IBRV, PI$_3$V, BVDV—are inactivated both by BACI and acriflavine, the inactivation by BACI being somewhat greater. The naked virus BPV is inactivated by acriflavine, but not by BACI alone.

After virus inactivation by means of acriflavine and BACI was detected in EME medium, it was checked whether these substances can also inactivate virus in protein-containing solutions. The following protein solutions were treated with the virus species indicated:

| | |
|---|---|
| Beriplex ® | PPV |
| Horse serum | BVDV, BPV |
| Beriate ® | BVDV, BPV, BAV-1, Reo 3, IBRV |
| Haemate ® | PPV, Reo 3 |
| Venimmun ® | BVDV, PPV, CPV |
| FCS | CPV |
| Egg allantoic fluid | Influenza A, Influenza B |

The results obtained in these experiments are shown in tabular form below.

Example 4
Virus Inactivation with Acridines and Benzalkonium Chloride in Protein Solutions As emerges from the results in Table 4, it is possible to inactivate completely different viruses in a methodologically simple manner in protein solutions using acridines and/or benzalkonium chloride. It appears clear here, however, that by means of benzalkonium chloride alone only envelope-containing viruses can be inactivated, whereas by means of acridines both envelope-containing and also nonenveloped virus species are inactivated. Both substances act synergistically in their virucidal action, i.e. the magnitude of the, virus inactivation with the combination acriflavine+ benzalkonium chloride is higher than with the two individual substances.

The results in Table 4 also show that virus inactivation in protein solutions is dependent on:
1. the virus species to be inactivated
2. the constituents and nature of the protein solution
3. the inactivating agent concentration
4. the inactivation time
5. the inactivation temperature.

The virus inactivation is also pH-dependent—results not shown. At a pH of below 5.5, virus inactivation takes place more slowly than at higher pHs.

Tables 5–7 contain the results of the biological activity of the protein solutions after virus inactivation by means of acriflavine and/or benzalkonium chloride. The biological activity was determined in Venimmun® by the content of antibodies before and after virus inactivation, and in Haemate®; Beriate® and Beriplex® by the determination of the clotting-promoting activity—measured in international units.

TABLE 4

Virus inactivation with acridines and benzalkonium chloride in protein solutions

| Protein solution and virus | Inactivating agent | Concentration (mg/ml) | Inactivation Temperature (° C.) | Inactivation time (h) | Control titer ($\log_{10}$/ml) | Treatment titer ($\log_{10}$/ml) | Titer reduction ($\log_{10}$/ml) |
|---|---|---|---|---|---|---|---|
| Horse serum + BPV | Acriflavine | 0.001 | 37 | 0 | 5.4 | 5.4 | 0 |
|  |  |  |  | 1 | 5.2 | ≦1.5 | ≧3.7 |
|  |  |  |  | 2 | 5.1 | ≦1.5 | ≧3.6 |
| Horse serum + BVDV | Acriflavine | 0.001 | 37 | 0 | 5.0 | 5.0 | 0 |
|  |  |  |  | 1 | 5.1 | ≦1.5 | ≧3.6 |
|  |  |  |  | 2 | 5.0 | ≦1.5 | ≧3.5 |
| Beriate + BPV | Acriflavine | 0.001 | 37 | 0 | 5.4 | 5.4 | 0 |
|  |  |  |  | 1 | 5.0 | ≦1.5 | ≧3.5 |
|  |  |  |  | 2 | 5.0 | ≦1.5 | ≧3.5 |
| Beriate + BVDV | Acriflavine | 0.001 | 37 | 0 | 5.0 | 5.0 | 0 |
|  |  |  |  | 1 | 5.0 | ≦1.5 | ≧3.5 |
|  |  |  |  | 2 | 4.8 | ≦1.5 | ≧3.5 |
| Beriate + Reo 3 | Ethacridine lactate | 0.3 | 45 | 0 | 5.4 | 5.1 | 0.3 |
|  |  |  |  | 1 | 4.7 | ≦1.5 | ≧3.2 |
|  |  |  |  | 2 | 4.7 | ≦1.5 | ≧3.2 |
| Beriate + IBR | Ethacridine lactate | 0.3 | 45 | 0 | 6.5 | 6.5 | 0 |
|  |  |  |  | 1 | 5.7 | 2.0 | 3.7 |
|  |  |  |  | 2 | 4.3 | ≦1.5 | ≧2.8 |

TABLE 4-continued

Virus inactivation with acridines and benzalkonium chloride in protein solutions

| Protein solution and virus | Inactivating agent | Concentration (mg/ml) | Inactivation Temperature (° C.) | Inactivation time (h) | Control titer ($\log_{10}$/ml) | Treatment titer ($\log_{10}$/ml) | Titer reduction ($\log_{10}$/ml) |
|---|---|---|---|---|---|---|---|
| Haemate + PPV | Acriflavine | 0.001 | 37 | 0 | 5.4 | 5.5 | 0 |
| | | | | 1 | 5.5 | 3.3 | 2.2 |
| | | | | 2 | 5.5 | 1.9 | 3.6 |
| | | | | 3 | 5.3 | ≦1.5 | ≧3.8 |
| Venimmun + PPV | Acriflavine | 0.001 | 37 | 0 | 4.0 | 4.0 | 0 |
| | | | | 1 | 3.9 | ≦1.5 | ≧2.4 |
| | | | | 2 | 3.9 | ≦1.5 | ≧2.4 |
| Venimmun + CPV | Acriflavine | 0.001 | 37 | 0 | 6.9 | 6.6 | 0.5 |
| | | | | 1 | 6.8 | 4.8 | 2.0 |
| | | | | 2 | 6.8 | 3.9 | 2.9 |
| | | | | 3 | 6.9 | 3.9 | 3.0 |
| Venimmun + BVDV | Acriflavine | 0.001 | 37 | 0 | 6.4 | 6.4 | 0 |
| | | | | 1 | 5.8 | 4.5 | 1.3 |
| | | | | 2 | 6.3 | 1.9 | 4.4 |
| | | | | 3 | 6.0 | 0 | ≧6.0 |
| Egg allantoic fluid + Influenza virus B | Acriflavine | 0.001 | 37 | 0 | 7.4 | 7.4 | 0 |
| | | | | 1 | 7.1 | 6.4 | 0.7 |
| | | | | 2 | 6.9 | 5.0 | 1.9 |
| Egg allantoic fluid + Influenza virus B | BACl | 0.02 | 37 | 0 | 7.4 | 7.4 | 0 |
| | | | | 1 | 7.1 | 6.0 | 1.1 |
| | | | | 2 | 6.9 | 3.6 | 3.3 |
| Egg allantoic fluid + Influenza virus B | Acriflavine + BACl | 0.001 0.02 | 37 | 0 | 7.4 | 7.4 | 0 |
| | | | | 1 | 7.1 | 4.1 | 3.0 |
| | | | | 2 | 6.9 | 2.5 | 4.4 |
| Beriplex + PPV | Acriflavine | 0.001 | 30 | 0 | 4.8 | 4.8 | 0 |
| | | | | 1 | 4.6 | 3.6 | 1.0 |
| | | | | 2 | 4.6 | 2.9 | 1.7 |
| | | | | 3 | 4.8 | ≦1.5 | ≧3.3 |
| Beriplex + PPV | BACl | 0.001 | 30 | 0 | 4.8 | 4.8 | 0 |
| | | | | 1 | 4.8 | 4.8 | 0 |
| | | | | 2 | 4.6 | 4.8 | 0 |
| | | | | 3 | 4.6 | 4.6 | 0 |
| Beriate + PPV | Acriflavine + BACl | 0.001 0.01 | 30 | 0 | 4.8 | 4.8 | 0 |
| | | | | 1 | 4.8 | 3.5 | 1.3 |
| | | | | 2 | 4.6 | ≦1.5 | ≧3.1 |
| | | | | 3 | 4.6 | ≦1.5 | ≧3.1 |
| Beriplex + PPV | Acriflavine | 0.001 | 37 | 0 | 4.8 | 4.8 | 0 |
| | | | | 1 | 4.6 | 2.0 | 2.6 |
| | | | | 2 | 4.6 | ≦1.5 | ≧3.1 |
| | | | | 3 | 4.8 | ≦1.5 | ≧3.3 |
| Beriplex + PPV | BACl | 0.01 | 37 | 0 | 4.8 | 4.8 | 0 |
| | | | | 1 | 4.6 | 4.6 | 0 |
| | | | | 2 | 4.6 | 4.6 | 0 |
| | | | | 3 | 4.8 | 4.6 | 0.2 |
| Beriplex + PPV | Acriflavine + BACl | 0.001 0.01 | 37 | 0 | 4.8 | 4.8 | 0 |
| | | | | 1 | 4.6 | 1.8 | 2.8 |
| | | | | 2 | 4.6 | ≦1.5 | ≧3.1 |
| | | | | 3 | 4.8 | ≦1.5 | ≧3.3 |
| FCS + CPV | Acriflavine | 0.001 | 37 | 0 | 6.6 | 6.6 | 0 |
| | | | | 1 | n.d. | 4.9 | 1.7 |
| | | | | 2 | n.d. | 4.0 | 2.6 |
| | | | | 3 | 6.9 | 3.4 | 3.5 |
| FCS + CPV | Acriflavine | 0.001 | 45 | 0 | 6.8 | 6.8 | 0 |
| | | | | 1 | n.d. | 4.8 | 2.0 |
| | | | | 2 | n.d. | 3.5 | 3.3 |
| | | | | 3 | 7.0 | 2.8 | 4.2 |

TABLE 5

Determination of the biological activity (antibody titer) in protein solutions before and after virus inactivation by means of acriflavine and benzalkonium chloride

| Protein solution | Name | Temperature and duration of the treatment | Reciprocal neutralization titer[1] against polio virus Type 1 | |
|---|---|---|---|---|
| | | | Without inactivating agent | With inactivating agent[2] |
| Low-cryo human plasma (individual plasma) | H1 | 37° C. 2 hours | 646 | 646 |
| | H2 | | 741 | 562 |
| | H3 | | 741 | 646 |
| | H4 | | 646 | 741 |
| | H5 | | 376 | 562 |
| Venimmun ® (Final product) various batches | V1 | 37° C. 2 hours | 2234 | 851 |
| | V2 | | 1950 | 1698 |
| | V3 | | 1698 | 1698 |
| | V4 | | 1698 | 1698 |
| | V5 | | 1479 | 1479 |
| Low-cryo human plasma (individual plasma) | H1 | 45° C. 2 hours | 427 | 977 |
| | H2 | | 1288 | 977 |
| | H3 | | 1288 | 977 |
| | H4 | | 977 | 1122 |
| | H5 | | 977 | 1288 |
| Venimmun ® (Final product) various batches | V1 | 45° C. 2 hours | 1950 | 2234 |
| | V2 | | 2570 | 2234 |
| | V3 | | 2234 | 1479 |
| | V4 | | 2234 | 1950 |
| | V5 | | 2234 | 1479 |

[1]Titer calculation according to Spearman-Karber from $\log_2$ dilution series using 8 replicates/dilution stage
[2]Acriflavine 0.001 mg/ml + BACl 0.02 mg/ml

TABLE 6

Determination of the biological activity (antibody titer in protein solutions before and after virus inactivation by means of acriflavine and benzalkonium chloride

| Protein solution | Name | Temperature and duration of the treatment | Rec. HAH anti-$PI_3$ virus Antibody titer[1] | | Rec. HAH anti-reo3 virus Antibody titer[1] | |
|---|---|---|---|---|---|---|
| | | | Without I.[2] | With I.[2] | Without I.[2] | With I.[2] |
| Low-cryo human plasma (individual plasma) | H1 | 45° C. 2 hours | 80 | 80 | 320 | 320 |
| | H2 | | 80 | 80 | 320 | 320 |
| | H3 | | 80 | 80 | 320 | 320 |
| | H4 | | 80 | 80 | 320 | 320 |
| | H5 | | 80 | 80 | 320 | 320 |
| Venimmun ® (Final product) various batches | V1 | 45° C. 2 hours | 320 | 320 | 320 | 320 |
| | V2 | | 320 | 320 | 320 | 320 |
| | V3 | | 320 | 320 | 320 | 320 |
| | V4 | | 320 | 320 | 320 | 320 |
| | V5 | | 320 | 320 | 320 | 320 |
| Horsye serum (individual sera) | P1 | 45° C. 2 hours | n.d. | n.d. | 640 | 640 |
| | P2 | | | | 640 | 640 |
| | P3 | | | | 640 | 640 |
| | P4 | | | | 640 | 640 |
| | P5 | | | | 640 | 640 |

[1]Titer determination in $\log_2$ dilution series
[2]I. = inactivating agents: acriflavine 0.001 mg/ml + BACl 0.02 mg/ml

TABLE 7

Determination of the biological activity (clotting activity) of protein solutions before and after virus inactivation by means of acriflavine (A) and benzalkonium chloride (BACL)

| Protein solution | Temperature and duration of the treatment | Inactivating agent | Inactivating agent concentration (mg/ml) | Activity (IU/ml) |
|---|---|---|---|---|
| cryo-protein solution after Al(OH)$_3$ + QAE treatment | 3 hours 45° C. | A | 0.01 | 3.9 |
| | | A | 0.03 | 4.2 |
| | | A | 0.001 | 4.4 |
| | | BACl | 0.1 | 6.9 |
| | | BACl | 0.05 | 6.1 |
| | | A + BACl | 0.001 + 0.05 | 4.1 |
| | | Control | 0 | 5.3 |
| Haemate ® Factor VIII | 3 hours 37° C. | A | 0.002 | 18.9 |
| | | A | 0.001 | 16.8 |
| | | BACl | 0.02 | 20.7 |
| | | A + BACl | 0.001 + 0.02 | 17.6 |
| | | Control | 0 | 24.1 |
| Beriplex ® Factor II | 3 hours 37° C. | A | 0.002 | 48.8 |
| | | A | 0.001 | 50.0 |
| | | BACl | 0.02 | 61.3 |
| | | A + BACl | 0.001 + 0.02 | 47.9 |
| | | Control | 0 | 68.6 |

As emerges from the results in Tables 5 and 6, the content of neutralizing (Polio Type 1) and hemagglutination-inhibiting (HAH) antibodies ($PI_3$—and Reo 3 virus) in Venimmun® is not affected to an extent-exceeding the test variations (as a rule ±1 $\log_2$ stage) during virus inactivation by means of acridines and benzalkonium chloride. The activity decrease with the clotting preparations (Beriate®, Haemate®, Beriplex®) after acridines/benzalkonium chloride, inactivation is tolerable (Table 7).

What is claimed is:

1. A process for inactivating viruses, comprising:
   (a) forming a composition by adding acridine or an acridine derivative to a material suspected to contain viruses, wherein the acridine or acridine derivative is present at non-cytotoxic concentrations; and
   (b) incubating the composition of step (a) in vitro;
   wherein the acridine derivative is selected from the group consisting of ethacridine, 9-aminoacridine, 3,6-acridinediamine, acrisorcin acrizane, acridine orange, quinacrine, acricide, acridone, acridine-9-carboxylic acid, acranil, phenosafranin, phenoxazine, phenothiazine, acriflavine, and salts thereof.

2. The process as claimed in claim 1, wherein the material further comprises at least one protein, wherein the protein retains its biological activity.

3. The process as claimed in claim 1, wherein said process is performed at a temperature of 20–60° C.

4. The process as claimed in claim 1, wherein said process is performed at a temperature of 25–37° C.

5. The process as claimed claim 1, wherein said process is performed at pH 5–9.

6. The process as claimed in claim 1, wherein said acridine or acridine derivative is present at a concentration of 0.0001 to 1.0 g/l.

7. The process as claimed in claim 6, wherein said acridine or acridine derivative is present at a concentration of 0.0005 to 0.1 g/l.

8. The process as claimed in claim 1, wherein said process is performed for 0.5 to 10 hours.

9. The process as claimed in claim 8, wherein said process is performed for 2 to 5 hours.

10. The process as claimed in claim 1, wherein the viruses are nonenveloped viruses.

11. The process as claimed in claim 1, wherein the viruses are enveloped viruses.

12. A process for inactivating viruses, comprising:
    (a) forming a composition by adding benzalkonium chloride and acridine or an acridine derivative to a material suspected to contain viruses, wherein the benzalkonium chloride is present at a concentration up to 0.1 g/l and the acridine or acridine derivative is present at non-cytotoxic concentrations; and
    (b) incubating the composition of step (a) in vitro,
    wherein the material further comprises at least one protein that retains its biological activity.

13. The process as claimed in claim 12, wherein said process is performed at a temperature of 20–60° C.

14. The process as claimed in claim 12, wherein said process is performed at a of 25–37° C.

15. The process as claimed in claim 12, wherein said process is performed at pH 5–9.

16. The process as claimed in claim 12, wherein said acridine or acridine derivative is present at a concentration of 0.0001 to 1.0 g/l.

17. The process as claimed in claim 16, wherein said acridine or acridine derivative is present at a concentration of 0.0005 to 0.1 g/l.

18. The process as claimed in claim 12, wherein said benzalkonium chloride is present at a concentration of 0.004 to 0.1 g/l.

19. The process as claimed in claim 18, wherein said benzalkonium chloride is present at a concentration of 0.01 to 0.05 g/l.

20. The process as claimed in claim 12, wherein said process is performed for 0.5 to 10 hours.

21. The process as claimed in claim 20, wherein said process is performed for 2 to 5 hours.

22. The process as claimed in claim 12, wherein the viruses are nonenveloped viruses.

23. The process as claimed in claim 12, wherein the viruses are enveloped viruses.

* * * * *